United States Patent [19]

Schilder

[11] Patent Number: 5,017,138

[45] Date of Patent: May 21, 1991

[54] SET OF ENDODONTIC INSTRUMENTS

[76] Inventor: Herbert Schilder, 12 Lorna Road, Newton, Mass. 02159

[21] Appl. No.: 347,714

[22] Filed: May 5, 1989

[51] Int. Cl.$^5$ .............................................. A61C 5/02
[52] U.S. Cl. .................................................... 433/102
[58] Field of Search ........................................ 433/102

[56] References Cited

U.S. PATENT DOCUMENTS 4,332,561  1/1982  McSpadden .................. 433/102
4,518,356  5/1985  Green .......................... 433/102

OTHER PUBLICATIONS

Pfingst Catalog, No. 33, 1983, p. 21.

Primary Examiner—Cary E. Stone
Attorney, Agent, or Firm—Wolf, Greenfield & Sacks

[57] ABSTRACT

Differences in the diameters of successive cutting instruments, either hand- or engine-powered, within sets of instruments described herein progress sequentially by constant percentages of increase, rather than by constant linear increase as is currently the practice in the dental manufacturing industry.

15 Claims, 1 Drawing Sheet

SET OF ENDODONTIC INSTRUMENTS

SUBJECT MATTER OF INVENTION

The present invention relates to an improved set of endodontic instruments, and in particular to an improved set of reamers, files and shapers.

BACKGROUND OF INVENTION

The standardization of endodontic instruments is considered important by endodontists since it assures them of optimal selection, uniform availability, convenience and comparability of such endodontic instruments. Over the years, the industry has developed several standards for root canal instruments and in particular for reamers and files. The industry use ISO standard 3630 to define all standard instruments for root canal preparation. Among other things, shapes, profiles, lengths, sizes, acceptable manufacturing tolerances and minimum requirements of mechanical stress are carefully defined, as are other factors such as color codes. The ISO standard 3630 was established by the Technical Committee 106, of the International Standardization Organization. Pursuant to these standards, an international order numbering system has been developed by which defined sizes for reamers and files are identified. Because such accepted standards have been so ingrained in the practice of endodontics, efforts have been limited in the reexamination of some of the principles upon which these standards have been based. Specifically, the use of reamers and files in endodontics conventionally begins with an instrument having a small diameter. As the endodontist works on a root canal to properly shape and enlarge it, larger instruments are substituted as the endodontist's work progresses. The gradation of increased sizes has become part of the standardization established under the ISO standards. Specifically, the diameters of the cones of successively larger reamers or files are increased under ISO standard sizes, from 0.10 mm to 0.60 mm in uniformly incremental steps of 0.05 mm and in sizes from 0.60 mm to 1.40 mm in uniformly incremental steps of 0.10 mm. These incremental steps are made with acceptable deviations of plus or minus 0.02 mm. Conventionally available standard sets of reamers, files and shapers are all incrementally larger from one to the next larger one by exactly the same absolute dimension. The incremental increases are the same as each larger instrument is used. Thus, the ratio of material removed to the diameter of the canal is much greater at the beginning of the treatment when the canal is small than it is when the larger tools are used towards the end of the reaming or filing process. Accordingly, the necessary delicate feel of the endodontist is impaired by the relatively large incremental steps at the beginning and is less than satisfactory with existing sets of files and reamers. This lack of appropriate feel is particularly apparent in smaller diameter instruments in which, for instance, there is a 50% increase from the 0.10 mm to the 0.15 mm reamer under the ISO standards. This difference is not altogether satisfactory because this change in size does not permit an endodontist a proper control in the deep narrow portions of root canals.

Reference to the use of sets of reamers or files do not consider problems inherent in the absolute diameter differentials between adjacent instruments. For example, U.S. Pat. No. 4,536,159 simply makes reference to the use of sets with uniform 0.05 mm diameter differentials as typically used in preparing the root canal. Other references such as U.S. Pat. Nos. 4,538,989, 4,340,364, 4,332,561 and 4,674,979 either have similarly limited references or do not even discuss the use of endodontic tools such as reamers or files in sets.

BRIEF SUMMARY OF INVENTION

The present invention recognizes the importance of utilizing a set of endodontic instruments, such as files or reamers, as a set in a manner which permits the endodontist to prepare a root canal effectively and with maximum sensitivity and flexibility. In the present invention there is provided a set of instruments in which the size from the smallest to the largest increases in uniformly constant incremental percentages. Thus for example, the increase in a reamer or file size is at a uniform percentage, rather than at a uniform 0.05 mm increase in diameter. In a typical set of six files with the smallest 0.10 mm diameter each of the six increases over the next smallest by exactly the same diameter percentage. Similar uniform incremental changes occur in sets having greater than six instruments. Thus, in the present invention there is provided a plurality of individual elongated endodontic cutting instruments as a set in which each differs in size at corresponding diameters of a cutting section at a constant percentage ratio of one instrument to the next larger instrument.

Root canals are rarely parallel and rarely straight. They tend to taper toward the root apex, being generally narrower in the apical third of the root, and greatly wider in the coronal third of the root. They tend to have curvatures which, while occurring potentially anywhere along the lengths of the canal, tend to be more common and more pronounced in the deeper, more apical portion of the canal. These naturally occurring realities of root canal shape, taper and tortuosity, sometimes severe, make manipulations in the apical portion of root canals more difficult and complex than manipulations in the coronal portions of root canals, which tend to be wider and straighter.

Manipulation in the apical portion of root canals is aided by the use of more flexible, more finely graded instruments, which allow for more delicate feel by the dentist.

Root canal enlarging instruments manufactured in accordance with the present invention provide fine percentage gradations where they are most needed (and do not currently exist) in smaller sizes of any given set, and few gradations where they are least needed (and do presently exist) in larger sizes.

Thus, use of these instruments provide faster, more controlled, and more effective cleaning and shaping of root canals with the use of fewer instruments.

DESCRIPTION OF DRAWINGS

The present invention will be more clearly understood when considered in connection with the accompanying drawings in which.

DETAILED DESCRIPTION OF THE INVENTION

Figures 1, 1A:
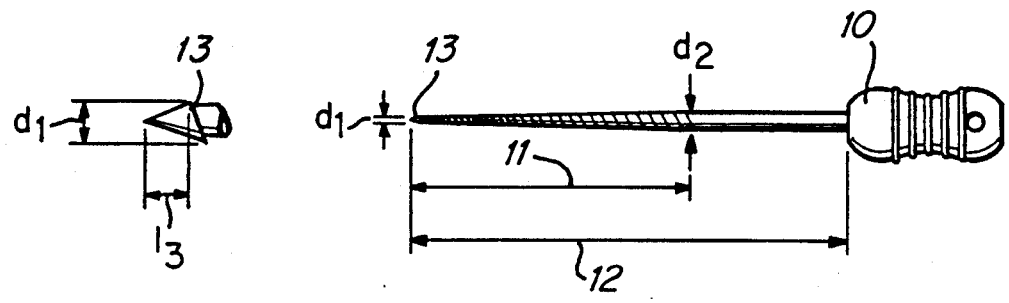
FIG. 1 is a plan view of a file which may comprise a component of the invention.
FIG. 1A is an enlarged detail of a part of FIG. 1.

The present invention is described in connection with the accompanying drawings which illustrate a typical file adapted and used in a set of six in relative dimensions which embody the present invention. However, the principles of the present invention may also be applied to any elongated cutting, shaping, or abrading endodontic instruments, both hand and engine powered. As illustrated in the present invention each instrument is conventionally made using conventional technology. Thus, the cutting edge of the instrument may be made by grinding an elongated blank or by twisting a blank having a polyhedric cross-section in accordance with well-known techniques. As illustrated, in the case of a file it includes a handle 10, with a working part 11, a working length 12, a tip 13, a cone diameter $d_1$ (as measured in hundredths of a millimeter, one millimeter from the cone tip), and a diameter $d_2$ at the end of the working part 11. $D_1$ identifies an instrument's size, i.e. 0.1=ten one-hundredths or #10; 0.15=fifteen one-hundredths or #15. D2 is, under ISO standards 0.3 mm wider than $d_1$ 16 mm from the tip. This determines the slope of the instrument. Every instrument has a constant taper between $d_1$ and $d_2$. For example, #45, which is 0.45 mm at $d_1$, is 0.75 at $d_2$. In the ordinary standard the length of the working part 11 is 16 mm minimum. In these instruments, too, the working parts are a minimum of 16 mm long. The working length $l_3$ of the tip 13 is always equal or less than the cone diameter $d_1$ of the tip as illustrated in FIG. 1A. For reamers and files, the measurement set forth above are always uniformly applied. For other types of instruments such as rasps, barbs, broaches, etc. these dimensions may vary, depending upon functional differences and constructional features of the devices.

Figure 2:
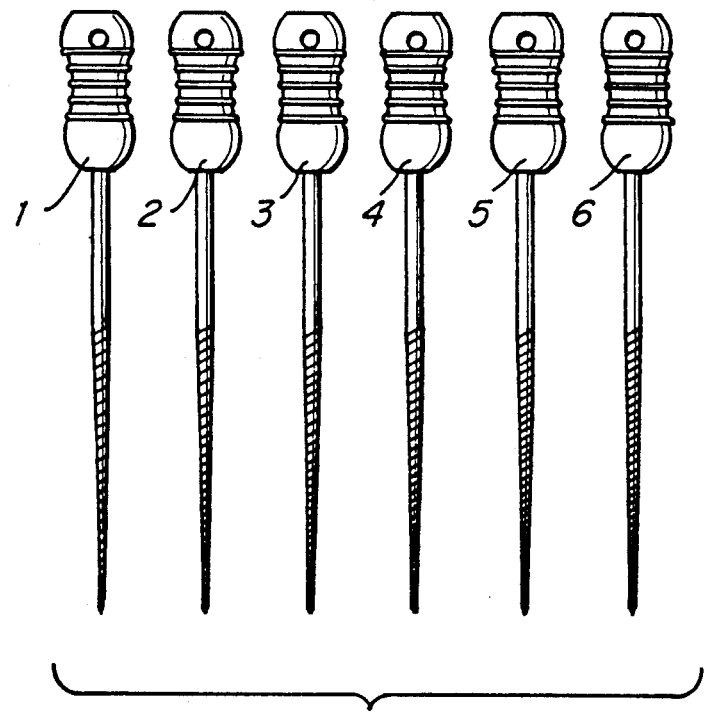
FIG. 2 is a somewhat schematic view of a set of six endodontic files illustrating the invention.

Under ISO standards, instruments having $d_1$ diameters between 0.10 mm and 0.60 mm increase linearly at 0.05. Thus eleven instruments span these sizes. In the embodiment of the invention illustrated in FIG. 2 which may be used in place of the ISO standard #10 to #60 instruments, there is illustrated a set of six endodontic instruments 1 to 6 inclusive with instrument 1 having the smallest diameter and increasing to the largest diameter instrument 6. The overall length of each instrument within the set is the same. In a typical set the working length 12 may be 25 mm. Within any set, however, the instruments may typically vary from 17 mm to 32 mm in their working length. The smallest diameter file in the embodiment illustrated has a d1 diameter of 0.10 mm±0.02 mm. Each larger diameter file in the set of six has a d1 diameter which is larger by 43.09691 percent than the next smaller one. Thus, instrument 2 has a d1 diameter of 0.143 mm±0.02 mm, instrument 3 has a d1 diameter of 0.205 mm±0.02 mm, instrument 4 has a d1 diameter of 0.293 mm±0.02 mm, instrument 5 has a d1 diameter of 0.419 mm±0.02 mm, and instrument 6 has a d1 diameter of 0.600 mm ±0.02 mm.

Similarly incremental changes in the uniform percentage basis may occur in sets of seven and sets of eight or more instruments. In a set of seven instruments between ISO sizes #10 and #60, the incremental increase is 34.8% while the incremental increase in the set of eight reamers is 29.17% in order to provide the smallest working tool with a d1 diameter of 0.10 mm and the largest with a d1 diameter of 0.60 mm. These incremental differences are reflected in the charts set forth below.

| Instrument | % d1 Increase | d1 diameter increase (mm) | d1 diameter (mm) |
|---|---|---|---|
| SET OF SIX INSTRUMENTS | | | |
| 1 | — | — | .100 mm |
| 2 | 43.09691% | .043 mm | .143 mm |
| 3 | 43.09691% | .0617 mm | .205 mm |
| 4 | 43.09691% | .0883 mm | .293 mm |
| 5 | 43.09691% | .1263 mm | .419 mm |
| 6 | 43.09691% | .1807 mm | .600 mm |
| SET OF SEVEN INSTRUMENTS | | | |
| 1 | — | — | .100 mm |
| 2 | 34.8% | .035 | .135 mm |
| 3 | 34.8% | .047 | .182 mm |
| 4 | 34.8 | .063 | .245 mm |
| 5 | 34.8 | .085 | .330 mm |
| 6 | 34.8 | .115 | .445 mm |
| 7 | 34.8 | .155 | .6 mm |
| SET OF EIGHT INSTRUMENTS | | | |
| 1 | — | — | .100 mm |
| 2 | 29.17 | .029 | .129 mm |
| 3 | 29.17 | .038 | .167 mm |
| 4 | 29.17 | .049 | .216 mm |
| 5 | 29.17 | .063 | .297 mm |
| 6 | 29.17 | .087 | .366 mm |
| 7 | 29.17 | .107 | .473 mm |
| 8 | 29.17 | .138 | .601 mm |

Although instruments between d1 diameter sizes 0.10 and 0.60 are conventionally the most frequently used, occasionally smaller or larger instruments are desirable. Thus, there may be occasions when an ISO size as low as 0.06 mm or as great as 1.40 mm d1 diameter is desired. Under those requirements, sets may be designed using the principle outlined, by making each larger diameter instrument larger by a constant d1 diameter percentage. Under such circumstances, a set of eight may be expanded to a set of 13 instruments by adding instruments having both smaller and larger d1 diameters. Such a set is reflected in the following chart.

| Instrument | % d1 Increase | d1 diameter increase (mm) | d1 diameter (mm) |
|---|---|---|---|
| SET OF THIRTEEN INSTRUMENTS | | | |
| 1 | — | — | .060 mm |
| 2 | 29.17 | .017 | .077 mm |
| 3 | 29.17 | .023 | .100 mm |
| 4 | 29.17 | .029 | .129 mm |
| 5 | 29.17 | .038 | .167 mm |
| 6 | 29.17 | .049 | .216 mm |
| 7 | 29.17 | .063 | .297 mm |
| 8 | 29.17 | .087 | .366 mm |
| 9 | 29.17 | .107 | .473 mm |
| 10 | 29.17 | .128 | .601 mm |
| 11 | 29.17 | .174 | .775 mm |
| 12 | 29.17 | .225 | 1.000 mm |
| 13 | 29.17 | .293 | 1.293 mm |

It is apparent than the principle may be applied to any reasonable number of instruments in a set with starting and ending $d_1$ diameters as may be desired.

It has been found that the use of these sets significantly increase the flexibility, control and ease of use of the instrument in enlarging the root canal. They are particularly useful in the apical ⅓ of the canal.

What is claimed is:

1. A set of elongated endodontic cutting instruments with each having different cutting diameters wherein said diameters increase from the smallest to the largest at a constant percentage of the diameter.

2. A set of endodontic elongated cutting instruments as set forth in claim 1 wherein said diameters are the d1 diameter as defined by ISO standards.

3. A set of endodontic elongated cutting instruments as set forth in claim 1 wherein said diameters are files.

4. A set of endodontic elongated cutting instruments as set forth in claim 1 wherein said diameters are reamers.

5. A set of endodontic elongated cutting instruments as set forth in claim 1 wherein said constant percentage is 43.1%.

6. A set of instruments as set forth in claim 5 having six instruments.

7. A set of instrument as set forth in claim 6 wherein the smallest instrument has a 0.100 mm d1 diameter.

8. A set of endodontic elongated cutting instruments as set forth in claim 1 wherein said constant percentage is 34.8%.

9. A set of instrument as set forth in claim 8 having seven instruments.

10. A set of instruments as set forth in claim 9 wherein the smallest instrument has a 0.100 mm d1 diameter.

11. A set of endodontic elongated cutting instruments as set forth in claim 1 wherein said constant percentage is 29.2%.

12. A set of instruments as set forth in claim 11 having eight instruments.

13. A set of instruments as set forth in claim 12 wherein the smallest instrument has a 0.100 mm d1 diameter.

14. A set of instruments as set forth in claim 1 wherein the largest instrument has a d1 diameter of substantially 0.600 mm and the smallest has a d1 diameter of 0.100 mm.

15. A method of shaping and enlarging a root canal of a human tooth comprising, successively inserting in the root canal for enlargement and shaping thereof a series of endodontic instruments having cutting surfaces in which the successive cutting instruments each has a d1 diameter, as determined by ISO standards, that is larger by a constant percentage than the previously inserted smaller instrument.

* * * * *